United States Patent
Chen et al.

(10) Patent No.: US 9,766,186 B2
(45) Date of Patent: Sep. 19, 2017

(54) ARRAY MODE REPEATER DETECTION

(71) Applicant: KLA-Tencor Corporation, Milpitas, CA (US)

(72) Inventors: Hong Chen, San Ramon, CA (US); Kenong Wu, Davis, CA (US); Eugene Shifrin, Sunnyvale, CA (US); Masatoshi Yamaoka, Tokyo (JP)

(73) Assignee: KLA-Tencor Corp., Milpitas, CA (US)

( * ) Notice: Subject to any disclaimer, the term of this patent is extended or adjusted under 35 U.S.C. 154(b) by 98 days.

(21) Appl. No.: 14/674,856

(22) Filed: Mar. 31, 2015

(65) Prior Publication Data

US 2016/0061749 A1    Mar. 3, 2016

Related U.S. Application Data (60) Provisional application No. 62/042,251, filed on Aug. 27, 2014.

(51) Int. Cl.
  *G01N 21/95* (2006.01)
  *G01N 21/00* (2006.01)
  *G01N 21/94* (2006.01)

(52) U.S. Cl.
  CPC ......... *G01N 21/9501* (2013.01); *G01N 21/00* (2013.01); *G01N 21/94* (2013.01); *G01N 21/95* (2013.01); *G01N 2201/061* (2013.01); *G01N 2201/10* (2013.01)

(58) Field of Classification Search
  CPC .................................................... G01N 21/88
  USPC .... 356/237.1–241.6, 242.1–243.8, 426–431, 356/600–640
  See application file for complete search history.

(56) References Cited

U.S. PATENT DOCUMENTS

| | | | |
|---|---|---|---|
| 4,644,172 A * | 2/1987 | Sandland ......... | G01N 21/95607 250/548 |
| 5,808,735 A * | 9/1998 | Lee .................... | G01N 21/9501 250/559.42 |
| 5,859,698 A * | 1/1999 | Chau ................ | G01N 21/95607 356/237.2 |

(Continued)

FOREIGN PATENT DOCUMENTS

| | | |
|---|---|---|
| EP | 2195834 | 6/2010 |
| JP | 2004-177139 | 6/2004 |
| JP | 2008-014650 | 1/2008 |

OTHER PUBLICATIONS

International Search Report for PCT/US2015/047139 mailed Dec. 14, 2015.

*Primary Examiner* — Tri Ton
*Assistant Examiner* — Jarreas C Underwood
(74) *Attorney, Agent, or Firm* — Ann Marie Mewherter (57) ABSTRACT

Systems and methods for detecting defects on a wafer are provided. One method includes generating test image(s) for at least a portion of an array region in die(s) on a wafer from frame image(s) generated by scanning the wafer with an inspection system. The method also includes generating a reference image for cell(s) in the array region from frame images generated by the scanning of the wafer. In addition, the method includes determining difference image(s) for at least one cell in the at least the portion of the array region in the die(s) by subtracting the reference image from portion(s) of the test image(s) corresponding to the at least one cell. The method further includes detecting defects on the wafer in the at least one cell based on the difference image(s).

34 Claims, 2 Drawing Sheets

(56) References Cited

U.S. PATENT DOCUMENTS

| | | | | |
|---|---|---|---|---|
| 5,864,394 | A * | 1/1999 | Jordan, III | G01N 21/94 257/E21.53 |
| 5,917,588 | A * | 6/1999 | Addiego | G01N 21/8806 356/237.2 |
| 6,031,607 | A * | 2/2000 | Miyazaki | G06T 7/001 250/550 |
| 6,392,749 | B1 * | 5/2002 | Meeks | G01B 11/065 356/634 |
| 7,127,098 | B2 * | 10/2006 | Shimoda | G01N 21/95684 250/208.1 |
| 7,339,661 | B2 * | 3/2008 | Korngut | G01N 21/47 250/234 |
| 7,345,754 | B1 * | 3/2008 | Zhao | G01N 21/4738 356/237.1 |
| 7,379,175 | B1 * | 5/2008 | Stokowski | G01N 21/95607 356/237.5 |
| 7,440,607 | B1 * | 10/2008 | Lin | G01N 21/8851 382/149 |
| 7,570,800 | B2 | 8/2009 | Lin et al. | |
| 7,664,608 | B2 * | 2/2010 | Urano | G01N 21/4738 356/237.1 |
| 7,751,046 | B2 * | 7/2010 | Levy | G01N 21/211 356/237.1 |
| 7,916,286 | B2 * | 3/2011 | Sali | G01N 21/95607 356/237.1 |
| 8,000,922 | B2 | 8/2011 | Chen et al. | |
| 8,041,106 | B2 | 10/2011 | Pak et al. | |
| 8,103,087 | B2 * | 1/2012 | Maeda | G06K 9/00557 348/25 |
| 8,111,900 | B2 | 2/2012 | Wu et al. | |
| 8,204,296 | B2 | 6/2012 | Bhaskar et al. | |
| 8,223,327 | B2 | 7/2012 | Chen et al. | |
| 8,467,047 | B2 | 6/2013 | Chen et al. | |
| 8,594,823 | B2 | 11/2013 | Park et al. | |
| 8,605,275 | B2 | 12/2013 | Chen et al. | |
| 8,692,878 | B2 | 4/2014 | Chen et al. | |
| 2003/0001598 | A1 * | 1/2003 | Weiner | G01R 31/307 324/754.22 |
| 2005/0232478 | A1 * | 10/2005 | Onishi | G06T 7/0004 382/149 |
| 2006/0078191 | A1 * | 4/2006 | Matsumura | G01N 21/8851 382/149 |
| 2007/0133860 | A1 * | 6/2007 | Lin | G06T 7/001 382/149 |
| 2010/0021041 | A1 | 1/2010 | Matsui et al. | |
| 2012/0070089 | A1 | 3/2012 | Yamada et al. | |

* cited by examiner

ARRAY MODE REPEATER DETECTION

BACKGROUND OF THE INVENTION

1. Field of the Invention

The present invention generally relates to systems and methods for detecting defects on a wafer, which are particularly useful for detecting repeating defects in array regions on the wafer.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

Some current inspection methods use standard images such as standard die images to detect repeater defects on wafers. Repeater defects are normally caused by foreign objects on a reticle/mask. After a wafer is printed with this kind of reticle, the defect appears on all dies. A die-to-die comparison inspection will fail because the defects on all dies will cancel each other resulting in weak or no signal from the defect. A standard die image (also commonly referred to as a "golden die") may be compared to a test die image acquired for a wafer being inspected and the results of the comparison may be input to a defect detection algorithm or method to determine if any defects are present in the test die. Such golden die images are commonly used for inspection of logic regions of dies since the logic regions of dies often do not include periodically repeating features that can be compared to one another for defect detection.

A disadvantage of using a standard die image for inspection is that, if the standard die image was acquired from a wafer other than the one being inspected, wafer-to-wafer noise can be relatively high and can interfere with defect detection or decrease the sensitivity of defect detection. In addition, if the standard die image is acquired using the same wafer that is being inspected, die-to-die noise can also interfere with, or decrease sensitivity of, defect detection. Furthermore, if the standard die image is generated using design data for the wafer, the standard die image may not adequately represent noise sources on the wafer thereby having the same disadvantages described above.

Accordingly, it would be advantageous to develop systems and methods for detecting defects on a wafer that do not have one or more of the disadvantages described above.

SUMMARY OF THE INVENTION

The following description of various embodiments is not to be construed in any way as limiting the subject matter of the appended claims.

One embodiment relates to a computer-implemented method for detecting defects on a wafer. The method includes generating one or more test images for at least a portion of an array region in one or more dies on a wafer from one or more frame images generated by scanning the wafer with an inspection system. The method also includes generating a reference image for one or more cells in the array region from two or more of the frame images generated by the scanning of the wafer with the inspection system. In addition, the method includes determining one or more difference images for at least one cell in at least the portion of the array region in the one or more dies by subtracting the reference image from one or more portions of the one or more test images corresponding to the at least one cell. The method further includes detecting defects on the wafer in the at least one cell based on the one or more difference images determined for the at least one cell. Generating the one or more test images, generating the reference image, determining the one or more difference images, and detecting the defects are performed with a computer system.

Each of the steps of the method may be further performed as described herein. In addition, the method may include any other step(s) of any other method(s) described herein. Furthermore, the method may be performed by any of the systems described herein.

Another embodiment relates to a non-transitory computer-readable medium storing program instructions executable on a computer system for performing a computer-implemented method for detecting defects on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to detect defects on a wafer. The system includes an inspection subsystem configured to scan a wafer to thereby generate frame images for the wafer. The system also includes a computer subsystem configured for performing the steps of the method described above. The system may be further configured as described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein relate to computer-implemented methods for detecting defects on a wafer. The embodiments described herein are particularly advantageous for detecting array repeater defects on wafers. In this manner, defect detection algorithm(s) that are configured to perform the method embodiments described herein may be referred to as array mode repeater algorithms. The term "array region" refers to the area in a die where the wafer pattern repeats periodically. The basic repeating pattern is called a "cell." Array regions are usually inspected by a cell-to-cell comparison instead of a die-to-die comparison. Die repeating defects may be detected at the same within die location in multiple frame images generated for different dies on the wafer. Die repeaters may be located in the array region of dies on the wafer. Due to severe noise in this region of the dies, array mode detection (commonly performed by cell-to-cell comparisons) does not have relatively high sensitivity for detecting the array repeaters. As will be described further herein, however, the embodiments described herein can be used to detect defects in the array region with higher sensitivity than that achievable by currently used systems and methods.

Figure 1:
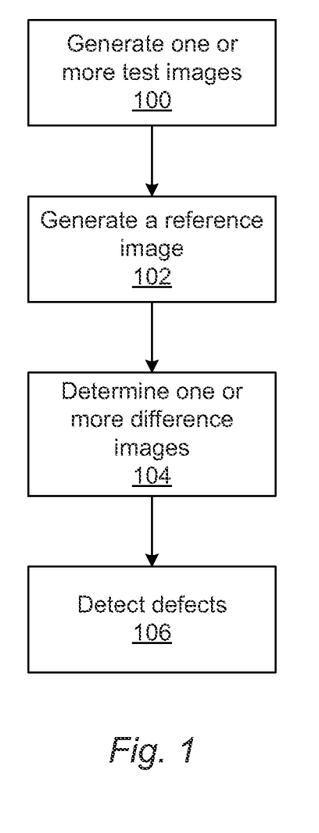
FIG. 1 is a flow chart illustrating one embodiment of a computer-implemented method for detecting defects on a wafer.

The method includes generating one or more test images, as shown in step 100 of FIG. 1, for at least a portion of an array region in one or more dies on a wafer from one or more frame images generated by scanning the wafer with an inspection system. The one or more dies may include any suitable number of dies on the wafer. For example, the one or more dies may include all of the dies in a row on the wafer, which may generally include from 3 or more dies. The array region in the one or more dies may have any suitable configuration known in the art and may be identified in the dies in any suitable manner (e.g., based on a design for the wafer and/or based on pattern characteristics in output (e.g., images) for the wafer). Scanning the wafer may be performed as described further herein with an inspection system that may be configured as described further herein. In addition, the method may include acquiring the frame images by performing such scanning of a wafer or may acquire the frame images from a storage medium in which the frame images were stored (e.g., by the inspection system that performed the scanning).

In one embodiment, generating the one or more test images is performed such that differences between portions of the one or more test images corresponding to defects and portions of the one or more test images corresponding to noise are greater than the differences in the one or more frame images. For instance, generating test image(s) as described further herein can enhance the signal (from die repeaters) to noise (random defects and other noise) ratio. In one such instance, as described further herein, generating the one or more test images includes performing a robust averaging of multiple frame images. Although some embodiments are described herein with respect to robust averaging, the embodiments are not limited to using such averaging to generate the images that are used as test images. For example, the test images may be generated using any method or algorithm that can enhance the die repeater signal as described above, which may include generating a median image or an average image from the frame images, which is then used as the test image. In this manner, the test image(s) may include a die relative median image.

In one embodiment, generating the one or more test images includes determining a robust average image from two or more of the frame images. In general, a robust average may be generated by removing the pixels for one outlier and computing the average from the rest of the pixels. In some such embodiments, a detection job may include image frames from two or more dies in a row on a wafer. Therefore, generating the test image(s) may include using each of the image frames from all or some of the dies in a row on the wafer to generate an average test image. In this manner, generating the test image(s) may include determining a robust average of all input frames.

The robust average frame image may then be used to detect die repeaters as described further herein. Generating a robust average image as described herein enhances the die repeater signal. For example, robust averaging will generally reduce any signals that vary from die to die such as noise and signals from random defects while substantially maintaining any signals that are substantially the same from die to die such as signals from repeating defects. As such, the die repeater defect signal will be enhanced with respect to the random defect signals and noise that are present in each of the individual frames that are averaged. Therefore, using such an image as the test image for defect detection as described further herein increases the sensitivity of the defect detection.

In another embodiment, generating the one or more test images includes determining the one or more test images from two or more of the frame images, and the method includes aligning the two or more frame images to each other prior to generating the one or more test images. The method may therefore include frame-by-frame alignment followed by generating the test image(s) from the aligned frames. For example, for frame images that are acquired by scanning a row of dies on a wafer, the frame images may be aligned to one of the frame images that is acquired at the centermost die in the row. In this manner, all individual test frames may be aligned to the center test frame before generating the one or more test images as described herein (e.g., via averaging). In addition, all of the input images may be aligned to any other suitable common point (e.g., in a design for the wafer or on the wafer itself). Determining the one or more test images from two or more aligned frame images may be performed according to any of the embodiments described further herein.

Aligning the frame images prior to generating the test image(s) (e.g., by averaging) will increase the signal-to-noise ratio in the test image(s), which will produce higher signal-to-noise ratios in the difference image(s) determined as described herein. Since the difference image(s) are used as described further herein for defect detection, higher signal-to-noise ratios in the difference images will provide higher sensitivity for the defect detection.

In an additional embodiment, each of the one or more test images is generated from only one of the one or more frame images. For example, unlike some embodiments described above in which multiple frame images are used in combination to generate a single test image that is then used for defect detection, in some embodiments, the test images may simply include the frame images that were generated by the inspection system. In this manner, each of the test images used for other steps described herein may be generated from or correspond to only one of the frame images. In some such embodiments, the test images may include the frame images themselves. However, some processing (e.g., noise filtering) may be performed on the frame images, each of which can then be used as a test image in other steps described herein.

The method includes generating a reference image, as shown in step 102 of FIG. 1, for one or more cells in the array region from two or more of the frame images generated by the scanning of the wafer with the inspection system. Generating the reference image may be performed in a number of different manners as described herein, and the way in which the reference image is generated may vary depending on the image(s) that are used as the test image(s). The cell(s) in the array region may have any suitable configuration known in the art, and the cell(s) can be identified in the array region in any suitable manner (e.g., based on a design for the wafer or based on information about patterns formed in the dies on the wafer that can be determined from images of the wafer).

In one embodiment, generating the reference image for the one or more cells in the array region from the two or more frame images is performed such that portions of the two or more frame images corresponding to defects on the wafer are altered. In other words, some portions of the frame images that are responsive to defects on the wafer preferably look different in the reference image than in the frame images. The portions of the two or more frame images corresponding to the defects on the wafer are preferably altered such that signals or image data corresponding to all defects and all noise are substantially suppressed or minimized. For example, although some specific methods are described herein for generating a reference image (e.g., using a median of a robust average), the important features of these mathematical operations are that they can be used to substantially exclude outliers (defects) from the final reference image and substantially suppress random noise in the final reference image. Any other mathematical operation(s) (e.g., a robust harmonic average) that possesses these capabilities would work and might be useful in some cases.

In one embodiment in which generating the one or more test images includes determining a robust average image from two or more of the frame images, generating the reference image includes determining a median cell image from the robust average image. In this manner, the method may include determining a multiple cell median image from the robust average test image. As described above, generating a robust average test image will enhance the repeater defect signal with respect to random defect signals and noise in each of the test image frames. Therefore, random defects and noise may be substantially eliminated from the robust average test image. As such, the repeater defect signal in such a robust average test image will essentially be an outlier that can be removed from the robust average test image by generating a median image from the robust average test image. Consequently, signals from random defects and noise will be substantially suppressed in the reference image by the robust averaging used to generate the test image and signals from repeating defects will be substantially suppressed by taking the median of the robust averaged image. Such a median cell image will, therefore, make an excellent reference image for defect detection due to its substantially low noise and defect-free characteristics.

In an additional embodiment in which each of the one or more test images is generated from only one of the one or more frame images, generating the reference image includes determining a median cell image from at least one of the one or more frame images. For instance, for every frame image, a median cell image can be determined and used as the reference image. In particular, a reference image may be computed by a multiple cell median (or robust averaging) from only one test image (where the test image is computed by multiple die median (or robust averaging)) when that test image includes more than one (or many) cells. As described further herein, other mathematical operation(s) may also be used that can essentially remove defect information from the frame images.

In some embodiments, the one or more frame images used to generate the one or more test images and the two or more frame images used to generate the reference image are acquired in the same scan of the wafer performed during the scanning. In other words, all of the frame images used in the embodiments described herein to generate the test image(s) and the reference image may be acquired in only one scan of the wafer. Therefore, the embodiments described herein are different from some other wafer inspection methods that use standard reference dies (SRDs) because unlike those methods, which typically require two scans, the embodiments described herein may be performed using only one scan of a wafer. For example, some SRD-based methods include an SRD training scan and an SRD inspection scan. The training scan may be used to generate a standard reference from a known good wafer. The SRD inspection run then scans the wafer being inspected and compares the current scan image with the standard reference image generated during the SRD training scan. However, the embodiments described herein do not require any such SRD training scan. Instead, the embodiments described herein can scan a wafer once and perform defect detection using a single scan similar to die-to-die (random mode inspection) or cell-to-cell (array mode) inspection. For example, a robust average test such as that described herein and a reference image that is a multiple cell median image can be generated from the same wafer scan.

In another embodiment, at least one of the one or more frame images used to generate the one or more test images and at least one of the two or more frame images used to generate the reference image are acquired in the same scan of a single die on the wafer. For example, all of the frame images used to generate the test image(s) may be used to generate the reference image. In another example, at least some of the frame images used to generate the test image(s) may be used to generate the reference image. In this manner, images used to generate the test image(s) and the reference image may be acquired in the same die or dies on the wafer. In addition, images acquired in at least one die on the wafer may be used to generate both the test image(s) and the reference image. Therefore, the embodiments described herein are different from other methods that generate test images from a first portion of dies on a wafer and a reference image from a second portion of dies on the wafer that is different than the first portion. The embodiments are also different from other methods that generate test images from a die or dies on one wafer and a reference image from a die or dies on another wafer.

Using at least some images acquired in the same die or dies to generate both the test image(s) and the reference image is possible because generating the reference image as described herein results in suppression and/or elimination of repeater defect signals, random defect signals and noise in the resulting reference image. Using images from the same die or dies for both test image generation and reference image generation is advantageous because different scans are not required for generation of the test image(s) and the reference image, which increases the throughput of the inspection process as well as reduces the inspection system output that needs to be handled and processed by the inspection system. In addition, using at least some images acquired in the same die or dies may be particularly advantageous when there are variations across a wafer or wafers (e.g., process variations that cause color variations in the output of the inspection system) because in such situations, the variations may cause the reference image generated using an image of a die different from the die or dies used to generate the test image(s) to be a less than ideal reference image, which can then reduce the sensitivity of the inspection performed using the reference image. In contrast, since the embodiments described herein may use the same die or dies on the wafer for both test image generation and reference image generation, the wafer variation in the images used for both test image generation and reference image generation will be relatively low, which allows a particularly suitable reference image to be generated thereby enabling relatively sensitive inspection. Although it may be advantageous as described above to use the same die or dies for both test image generation and reference image generation, the embodiments described herein may also be performed such that the dies used for test image generation are different than (e.g., mutually exclusive of) the dies used for reference image generation.

The method also includes determining one or more difference images, as shown in step 104 of FIG. 1, for at least one cell in at least the portion of the array region in the one or more dies by subtracting the reference image from one or more portions of the one or more test images corresponding to the at least one cell. Determining the one or more difference images may be performed using any of the test and reference images described herein. For example, in one embodiment, determining the difference image(s) may include comparing a robust average test image with a multiple cell median image to detect die repeaters on the wafer. Since the reference image may be generated as described herein for a cell on the wafer and since the reference image may be subtracted from portion(s) of test image(s) corresponding to a cell on the wafer, generating the difference image(s) as described herein involves a cell-to-cell comparison. In addition, since the difference image(s) are used for defect detection as described further herein, the defect detection methods and systems described herein may be generally referred to as cell-to-cell defect detection methods and systems.

In an additional embodiment in which each of the one or more test images is generated from only one of the one or more frame images, determining the one or more difference images is performed by subtracting the reference image from the one or more portions of each of the one or more test images. In such an embodiment, the reference image may be a median cell image as described further herein. For example, for every frame image, a difference image may be determined using the frame image and the median cell image. In this manner, the difference image(s) may be generated by subtracting the median cell image from each of the test images, each of which was generated from only one of the frame images. Therefore, difference images may be generated for every cell. In other words, a difference image may be separately generated for each cell resulting in a one-to-one correspondence between difference images and cells. This embodiment is different than some other embodiments described herein in which the difference image is generated by subtracting the reference image from a test image generated from multiple frame images and therefore multiple cells. In this manner, the test images can be used collectively (e.g., as in a robust average test image) or singly (e.g., as multiple frame images) to determine only one difference image or multiple difference images.

The method further includes detecting defects, as shown in step 106 of FIG. 1, on the wafer in the at least one cell based on the one or more difference images determined for the at least one cell. For example, array mode defect detection may be performed using any of the difference images described herein. Detecting the defects based on the one or more difference images may be performed using any suitable defect detection method(s) and/or algorithm(s) known in the art. For example, median intensity values determined from a reference image generated as described herein may be plotted as a function of difference values in the one or more difference images to thereby generate a two-dimensional (2D) scatter plot. Outliers in the scatter plot may then be identified as corresponding to potential defects on the wafer. Existing defect detection algorithms such as the multi-die auto-thresholding (MDAT) algorithm that is used on some inspection systems that are commercially available from KLA-Tencor, Milpitas, Calif., may be used to perform such defect detection using scatter plots. In another example, signals in the difference image(s) may be compared to a threshold, and signals above the threshold may be identified as corresponding to defects while signals below the threshold may not be identified as corresponding to defects. However, the embodiments described herein are not limited in the types of defect detection methods and/or algorithms that can be used with the difference images described herein. For instance, the difference images determined as described herein can be input to any defect detection algorithm that accepts a difference image as input.

In one embodiment, the defects that are detected include defects that repeat in different cells at substantially the same within die location in two or more of the dies on the wafer. Since the test image is generated by robust averaging performed using multiple frame images in multiple dies, the detected defects are common for all of these dies and, therefore, reported as repeater defects for all of these dies. In this manner, the embodiments described herein can be used to detect die repeater defects in the array region of the dies. Detecting such defects is normally substantially difficult due to the noise that is usually present in inspection system output for the array region of dies. However, as described further herein, generating the test image(s) as described herein can enhance the signal-to-noise ratio for repeating defects and generating the reference image as described herein can suppress the signals from all defects and noise on the wafer. Therefore, using such test and reference images for defect detection as described herein provides substantially high sensitivity for detecting repeating defects including those located in the array region. The embodiments described herein are, therefore, particularly suitable for use in array mode repeater defect detection.

In one embodiment, detecting the defects includes determining an additional difference image from two or more of the difference images and detecting the defects based on the additional difference image. In one such embodiment, determining the additional difference image includes determining a robust average image from the two or more difference images. For example, in the embodiments in which the frame images themselves are used as the test images and a median cell image is used as the reference image, a difference image can be determined for each cell and then a robust average of all of the difference images may be generated. That robust average of the difference images may then be input to a defect detection step as described further herein, and defect detection may be performed as described further herein.

In another such embodiment, determining the additional difference image includes aligning the two or more difference images to each other and determining the additional difference image based on the aligned two or more difference images. For example, in embodiments described herein in which a difference image is determined for each cell, all of the difference images (or at least two of the difference images) for all of the cells (or at least two of the cells) may be aligned to each other and then a robust average image may be determined from the aligned difference images. Aligning the difference images to each other may include aligning all of the difference images to a common point (e.g., in the design for the wafer or based on patterns in the output generated for the wafer by the inspection system). In this case, difference images are being aligned rather than input images. Difference images do not have relatively sharp edges since the cell structure is the common pattern that is present in the median image and test image, which results in lower alignment/interpolation noise of the robust average difference image (compared to alignment of test images) and improves the signal-to-noise ratio for defect detection.

In some embodiments, the method includes identifying one or more of the at least one cell in which the defects are located based on the one or more frame images. In another embodiment, the detected defects are potential defects on the wafer, and the method includes determining a defect attribute for each of the potential defects and determining which of the at least one cell contains actual repeating defects based on the determined defect attributes corresponding to the at least one cell. For example, the method may include a post-processing step that determines the repeater signal on each die to find out which die(s) has or have the die repeater defect. In other words, the method may include computing a defect attribute for each repeater defect to indicate repeater signal from the frame images and reference images. The repeater signal value can be represented by a defect attribute. In one such example, the defect attribute calculation may include post-processing the defect patch on each frame from the dies included in a detection job to measure the repeater signal to determine whether the defect exists on each frame. Dies that have relatively strong signals at the identified repeater defect location may be identified as containing the repeater defect while dies that have relatively weak signals at the identified repeater defect location may be identified as not containing the repeater defect.

Generating the one or more test images, generating the reference image, determining the one or more difference images, and detecting the defects are performed with a computer system, which may be configured according to any of the embodiments described herein.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 2:
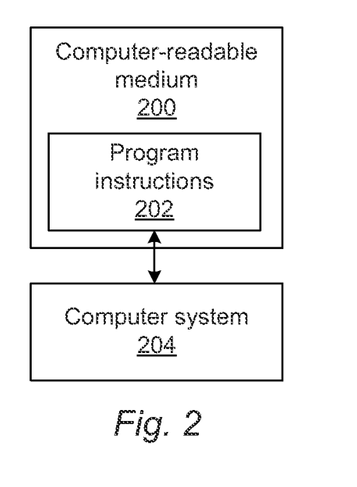
FIG. 2 is a block diagram illustrating one embodiment of a non-transitory computer-readable medium storing program instructions for causing a computer system to perform a computer-implemented method described herein.

Another embodiment relates to a non-transitory computer-readable medium storing program instructions executable on a computer system for performing a computer-implemented method for detecting defects on a wafer. One such embodiment is shown in FIG. 2. For example, as shown in FIG. 2, non-transitory computer-readable medium 200 stores program instructions 202 executable on computer system 204 for performing a computer-implemented method for detecting defects on a wafer. The computer-implemented method may include any step(s) of any method(s) described herein.

Program instructions 202 implementing methods such as those described herein may be stored on non-transitory computer-readable medium 200. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 204 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 3:
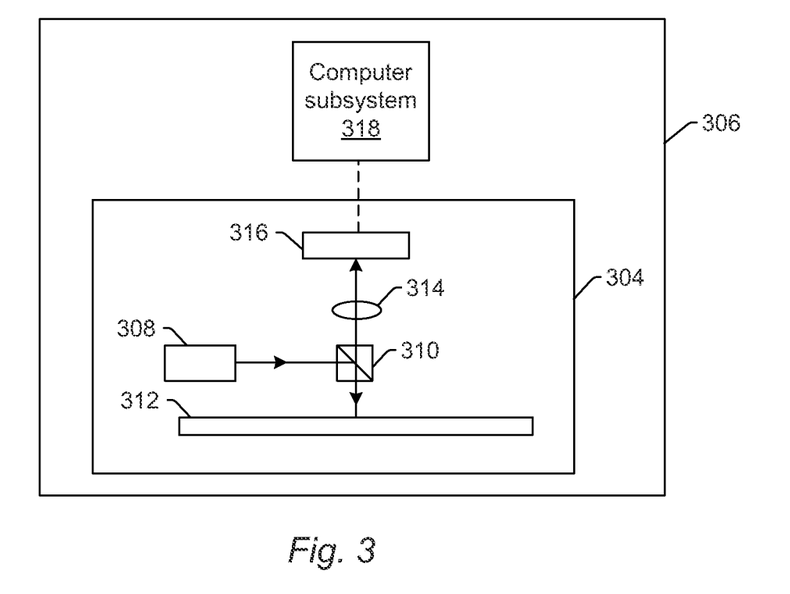
FIG. 3 is a schematic diagram illustrating a side view of an embodiment of a system configured to detect defects on a wafer.

An additional embodiment relates to a system configured to detect defects on a wafer. The system includes an inspection subsystem configured to scan a wafer to thereby generate frame images for the wafer. One embodiment of such an inspection subsystem is shown in FIG. 3 as inspection subsystem 304 of system 306. The inspection subsystem is configured to scan the wafer by scanning the wafer with light and detecting light from the wafer during the scanning. For example, as shown in FIG. 3, the inspection subsystem includes light source 308, which may include any suitable light source known in the art such as a broadband plasma light source.

Light from the light source may be directed to beam splitter 310, which may be configured to direct the light from the light source to wafer 312. The light source may be coupled to any other suitable elements (not shown) such as one or more condensing lenses, collimating lenses, relay lenses, objective lenses, apertures, spectral filters, polarizing components and the like. As shown in FIG. 3, the light may be directed to the wafer at a normal angle of incidence. However, the light may be directed to the wafer at any suitable angle of incidence including near normal and oblique incidence. In addition, the light or multiple light beams may be directed to the wafer at more than one angle of incidence sequentially or simultaneously. The inspection subsystem may be configured to scan the light over the wafer in any suitable manner.

Light from wafer 312 may be collected and detected by one or more detectors of the inspection subsystem during scanning. For example, light reflected from wafer 312 at angles relatively close to normal (i.e., specularly reflected light when the incidence is normal) may pass through beam splitter 310 to lens 314. Lens 314 may include a refractive optical element as shown in FIG. 3. In addition, lens 314 may include one or more refractive optical elements and/or one or more reflective optical elements. Light collected by lens 314 may be focused to detector 316. Detector 316 may include any suitable detector known in the art such as a charge coupled device (CCD) or another type of imaging detector. Detector 316 is configured to generate output that is responsive to the reflected light collected by lens 314. Therefore, lens 314 and detector 316 form one channel of the inspection subsystem. This channel of the inspection subsystem may include any other suitable optical components (not shown) known in the art. The output of the detector may include, for example, images, image data, signals, image signals, or any other output that can be generated by a detector suitable for use in an inspection system.

Since the inspection subsystem shown in FIG. 3 is configured to detect light specularly reflected from the wafer, the inspection subsystem is configured as a bright field (BF) inspection system. Such an inspection subsystem may, however, also be configured for other types of wafer inspection. For example, the inspection subsystem shown in FIG. 3 may also include one or more other channels (not shown). The other channel(s) may include any of the optical components described herein such as a lens and a detector, configured as a scattered light channel. The lens and the detector may be further configured as described herein. In this manner, the inspection subsystem may also be configured for dark field (DF) inspection.

The system also includes computer subsystem 318 that is coupled to the inspection subsystem such that the computer subsystem can receive frame images generated by the inspection subsystem. For example, the computer subsystem may be coupled to detector 316 and any other detectors included in the inspection subsystem such that the computer subsystem can receive frame image output generated by the detector(s). The computer subsystem is configured to perform the steps of the methods described herein including generating one or more test images, generating a reference image, determining one or more difference images, and detecting defects, according to any of the embodiments described herein. Computer subsystem 318 may be configured to perform any other steps described herein. The system shown in FIG. 3 may also be configured to perform any other steps described herein. The computer subsystem and the system may be further configured as described herein.

It is noted that FIG. 3 is provided herein to generally illustrate a configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection subsystem (e.g., by adding functionality described herein to an existing inspection system) such as the 29xx/28xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

Furthermore, although the system is described herein as being an optical or light-based inspection system, the inspection subsystem may be configured as an electron beam based inspection subsystem. The electron beam based inspection subsystem may be any suitable electron beam based inspection subsystem included in any suitable commercially available electron beam inspection system.

Further modifications and alternative embodiments of various aspects of the invention will be apparent to those skilled in the art in view of this description. For example, systems and methods for detecting defects on a wafer are provided. Accordingly, this description is to be construed as illustrative only and for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a wafer, comprising:
    generating one or more test images for at least a portion of an array region in one or more dies on a wafer from one or more of frame images generated by scanning the wafer with an inspection system;
    generating a reference image for one or more cells in the array region from two or more of the frame images generated by said scanning the wafer with the inspection system;
    determining one or more difference images for at least one cell in at least the portion of the array region in the one or more dies by subtracting the reference image from one or more portions of the one or more test images corresponding to the at least one cell; and
    detecting defects on the wafer in the at least one cell based on the one or more difference images determined for the at least one cell, wherein said generating the one or more test images, generating the reference image, determining the one or more difference images, and detecting the defects are performed with a computer system.

2. The method of claim 1, wherein generating the one or more test images comprises determining a robust average image from two or more of the frame images.

3. The method of claim 2, wherein generating the reference image comprises determining a median cell image from the robust average image.

4. The method of claim 1, wherein generating the one or more test images comprises determining the one or more test images from two or more of the frame images, and wherein the method further comprises aligning the two or more frame images to each other prior to generating the one or more test images.

5. The method of claim 1, wherein each of the one or more test images is generated from only one of the one or more of the frame images.

6. The method of claim 5, wherein generating the reference image comprises determining a median cell image from at least one of the one or more of the frame images.

7. The method of claim 5, wherein determining the one or more difference images is further performed by subtracting the reference image from the one or more portions of said each of the one or more test images.

8. The method of claim 1, wherein detecting the defects comprises determining an additional difference image from two or more of the difference images and detecting the defects based on the additional difference image.

9. The method of claim 8, wherein determining the additional difference image comprises determining a robust average image from the two or more difference images.

10. The method of claim 8, wherein determining the additional difference image comprises aligning the two or more difference images to each other and determining the additional difference image based on the aligned two or more difference images.

11. The method if claim 1, wherein generating the reference image for the one or more cells in the array region from the two or more of the frame images is performed such that portions of the two or more of the frame images corresponding to defects on the wafer are altered.

12. The method of claim 1, wherein the defects that are detected comprise defects that repeat in different cells at substantially the same within die location in two or more of the dies on the wafer.

13. The method of claim 1, wherein generating the one or more test images is performed such that differences between portions of the one or more test images corresponding to defects and portions of the one or more test images corresponding to noise are greater than the differences in the one or more frame images.

14. The method of claim 1, further comprising identifying one or more of the at least one cell in which the defects are located based on the one or more of the frame images.

15. The method of claim 1, wherein the detected defects are potential defects on the wafer, the method further comprising determining a defect attribute for each of the potential defects and determining which of the at least one cell contains actual repeating defects based on the determined defect attributes corresponding to the at least one cell.

16. The method of claim 1, wherein the one or more of the frame images used to generate the one or more test images and the two or more of the frame images used to generate the reference image are acquired in the same scan of the wafer performed during said scanning.

17. The method of claim 1, wherein at least one of the one or more of the frame images used to generate the one or more test images and at least one of the two or more of the frame images used to generate the reference image are acquired in the same scan of a single die on the wafer.

18. A non-transitory computer-readable medium, storing program instructions executable on a computer system for performing a computer-implemented method for detecting defects on a wafer, wherein the computer-implemented method comprises:
generating one or more test images for at least a portion of an array region in one or more dies on a wafer from one or more of frame images generated by scanning the wafer with an inspection system;
generating a reference image for one or more cells in the array region from two or more of the frame images generated by said scanning the wafer with the inspection system;
determining one or more difference images for at least one cell in at least the portion of the array region in the one or more dies by subtracting the reference image from one or more portions of the one or more test images corresponding to the at least one cell; and
detecting defects on the wafer in the at least one cell based on the one or more difference images determined for the at least one cell.

19. A system configured to detect defects on a wafer, comprising:
an inspection subsystem configured to scan a wafer to thereby generate frame images for the wafer, wherein the inspection subsystem comprises at least a light source and one or more detectors, wherein the inspection subsystem is further configured to direct light from the light source to the wafer, and wherein light from the wafer is collected and detected by the one or more detectors of the inspection subsystem during scanning to thereby generate the frame images; and
a computer subsystem configured for:
generating one or more test images for at least a portion of an array region in one or more dies on the wafer from one or more of the frame images;
generating a reference image for one or more cells in the array region from two or more of the frame images;
determining one or more difference images for at least one cell in at least the portion of the array region in the one or more dies by subtracting the reference image from one or more portions of the one or more test images corresponding to the at least one cell; and
detecting defects on the wafer in the at least one cell based on the one or more difference images determined for the at least one cell.

20. The system of claim 19, wherein generating the one or more test images comprises determining a robust average image from two or more of the frame images.

21. The system of claim 20, wherein generating the reference image comprises determining a median cell image from the robust average image.

22. The system of claim 19, wherein generating the one or more test images comprises determining the one or more test images from two or more of the frame images, and wherein the computer subsystem is further configured for aligning the two or more frame images to each other prior to generating the one or more test images.

23. The system of claim 19, wherein each of the one or more test images is generated from only one of the one or more of the frame images.

24. The system of claim 23, wherein generating the reference image comprises determining a median cell image from the two or more of the frame images.

25. The system of claim 23, wherein determining the one or more difference images is further performed by subtracting the reference image from the one or more portions of said each of the one or more test images.

26. The system of claim 19, wherein detecting the defects comprises determining an additional difference image from two or more of the difference images and detecting the defects based on the additional difference image.

27. The system of claim 26, wherein determining the additional difference image comprises determining a robust average image from the two or more difference images.

28. The system of claim 26, wherein determining the additional difference image comprises aligning the two or more difference images to each other and determining the additional difference image based on the aligned two or more difference images.

29. The system of claim 19, wherein generating the reference image for the one or more cells in the array region from the two or more of the frame images is performed such that portions of too or more of the frame images corresponding to defects on the wafer are altered.

30. The system of claim 19, wherein generating the one or more test images is performed such that differences between portions of the one or more test images corresponding to defects and portions of the one or more test images corresponding to noise are greater than the differences in the one or more of the frame images.

31. The system of claim 19, wherein the computer subsystem is further configured for identifying one or more of the at least one cell in which the defects are located based on the one or more of the frame images.

32. The system of claim 19, wherein the computer subsystem is further configured for determining a defect attribute for each of the detected defects and determining which of the at least one cell contains actual repeating defects based on the determined defect attributes corresponding to the at least one cell.

33. The system of claim 19, wherein the one or more of the frame images used to generate the one or more test images and the two or more of the frame images used to generate the reference image are acquired in the same scan of the wafer performed by the inspection subsystem.

34. The system of claim 19, wherein at least one of the one or more of the frame images used to generate the one or more test images and at least one of the two or more of the frame images used to generate the reference image are acquired in the same scan of a single die on the wafer.

* * * * *